(12) United States Patent
Fantuzzi et al.

(10) Patent No.: US 12,076,497 B2
(45) Date of Patent: *Sep. 3, 2024

(54) OVERMOLD TECHNIQUE FOR PEEL-AWAY INTRODUCER DESIGN

(71) Applicants: ABIOMED, Inc., Danvers, MA (US); Oscor, Inc., Palm Harbor, FL (US)

(72) Inventors: Glen Fantuzzi, Danvers, MA (US); Michael Tafone, Danvers, MA (US); Jeffrey Drum, Palm Harbor, FL (US)

(73) Assignees: ABIOMED, INC., Danvers, MA (US); OSCOR, INC., Palm Harbor, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,610

(22) Filed: Jun. 20, 2023

(65) Prior Publication Data
US 2024/0017037 A1 Jan. 18, 2024

Related U.S. Application Data

(63) Continuation of application No. 17/741,627, filed on May 11, 2022, now Pat. No. 11,717,640, which is a (Continued)

(51) Int. Cl.
*A61M 25/00* (2006.01)
*A61M 25/06* (2006.01)
(Continued)

(52) U.S. Cl.
CPC .... *A61M 25/0009* (2013.01); *A61M 25/0014* (2013.01); *A61M 25/0668* (2013.01);
(Continued)

(58) Field of Classification Search
None
See application file for complete search history.

(56) References Cited

U.S. PATENT DOCUMENTS

| 4,317,445 A | 3/1982 | Robinson |
| 4,380,252 A | 4/1983 | Gray et al. |

(Continued)

FOREIGN PATENT DOCUMENTS

| CN | 104623790 A | 5/2015 |
| EP | 77827 A1 | 5/1983 |

(Continued)

OTHER PUBLICATIONS

Decision to Grant received in corresponding Japanese Application No. 2019-551498 dated Sep. 1, 2021, 6 pp.
(Continued)

*Primary Examiner* — Jacob T Minskey
*Assistant Examiner* — Adrianna N Konves
(74) *Attorney, Agent, or Firm* — Botos Churchill IP Law LLP (57) ABSTRACT

A method for manufacturing a medical introducer includes placing an introducer sheath onto a mandrel, and overmolding an introducer hub onto a proximal end of the introducer sheath. The introducer sheath has one or more score lines formed on an inner surface and the mandrel has a number of surface protrusions so that when the introducer sheath is positioned on the mandrel, each of the surface protrusions contacts one of the score lines formed on the introducer sheath. The surface protrusions on the mandrel prevent plastic material from the introducer hub from contacting the score lines thereby maintaining the score lines during the overmolding.

22 Claims, 5 Drawing Sheets

Related U.S. Application Data continuation of application No. 15/834,783, filed on Dec. 7, 2017, now Pat. No. 11,364,363.

(60) Provisional application No. 62/431,671, filed on Dec. 8, 2016.

(51) Int. Cl.
- B29C 45/14 (2006.01)
- B29L 31/00 (2006.01)

(52) U.S. Cl.
 CPC .. B29C 45/14065 (2013.01); B29C 45/14336 (2013.01); *A61M 25/0097* (2013.01); *B29L 2031/7542* (2013.01)

(56) References Cited

U.S. PATENT DOCUMENTS

| | | |
|---|---|---|
| 4,402,685 A | 9/1983 | Buehler et al. |
| 4,569,347 A | 2/1986 | Frisbie |
| 4,651,751 A | 3/1987 | Swendson et al. |
| 4,699,611 A | 10/1987 | Bowden |
| 4,798,594 A | 1/1989 | Hillstead |
| 4,895,565 A | 1/1990 | Hillstead |
| 5,069,674 A | 12/1991 | Fearnot et al. |
| 5,139,486 A | 8/1992 | Moss |
| 5,180,372 A | 1/1993 | Vegoe et al. |
| 5,221,255 A | 6/1993 | Mahurkar et al. |
| 5,234,425 A | 8/1993 | Fogarty et al. |
| 5,250,033 A | 10/1993 | Evans et al. |
| 5,279,596 A | 1/1994 | Castaneda et al. |
| 5,304,142 A | 4/1994 | Liebl et al. |
| 5,312,355 A | 5/1994 | Lee |
| 5,320,611 A | 6/1994 | Bonutti et al. |
| 5,380,304 A | 1/1995 | Parker |
| 5,395,341 A | 3/1995 | Slater |
| 5,397,310 A | 3/1995 | Chu et al. |
| 5,397,311 A | 3/1995 | Walker et al. |
| 5,405,338 A | 4/1995 | Kranys |
| 5,407,430 A | 4/1995 | Peters |
| 5,409,463 A | 4/1995 | Thomas et al. |
| 5,409,469 A | 4/1995 | Schaerf |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,599,326 A | 2/1997 | Carter |
| 5,653,697 A | 8/1997 | Quiachon et al. |
| 5,713,867 A | 2/1998 | Morris |
| 5,752,937 A | 5/1998 | Otten et al. |
| 5,795,341 A | 8/1998 | Samson |
| 5,827,242 A | 10/1998 | Follmer et al. |
| 5,911,702 A | 6/1999 | Romley et al. |
| 5,935,122 A | 8/1999 | Fourkas et al. |
| 5,971,993 A | 10/1999 | Hussein et al. |
| 6,042,578 A | 3/2000 | Dinh et al. |
| 6,068,622 A | 5/2000 | Sater et al. |
| 6,080,141 A | 6/2000 | Castro et al. |
| 6,165,163 A | 12/2000 | Chien et al. |
| 6,197,014 B1 | 3/2001 | Samson et al. |
| 6,197,016 B1 | 3/2001 | Fourkas et al. |
| 6,217,565 B1 | 4/2001 | Cohen |
| 6,258,080 B1 | 7/2001 | Samson |
| 6,290,692 B1 | 9/2001 | Klima et al. |
| 6,319,244 B2 | 11/2001 | Suresh et al. |
| 6,338,730 B1 | 1/2002 | Bonutti et al. |
| 6,363,273 B1 | 3/2002 | Mastrorio et al. |
| 6,379,346 B1 | 4/2002 | McIvor et al. |
| 6,423,052 B1 | 7/2002 | Escano |
| 6,428,556 B1 | 8/2002 | Chin |
| 6,454,744 B1 | 9/2002 | Spohn et al. |
| 6,508,966 B1 | 1/2003 | Castro et al. |
| 6,544,270 B1 | 4/2003 | Zhang |
| 6,562,049 B1 | 5/2003 | Norlander et al. |
| 6,589,227 B2 | 7/2003 | Soenderskov |
| 6,613,038 B2 | 9/2003 | Bonutti et al. |
| 6,652,508 B2 | 11/2003 | Griffin et al. |
| 6,692,462 B2 | 2/2004 | Mackenzie et al. |
| 6,702,972 B1 | 3/2004 | Markle |
| 6,740,073 B1 | 5/2004 | Saville |
| 6,749,600 B1 | 6/2004 | Levy |
| 6,814,715 B2 | 11/2004 | Bonutti et al. |
| 6,824,553 B1 | 11/2004 | Samson et al. |
| 6,827,710 B1 | 12/2004 | Mooney et al. |
| 6,852,261 B2 | 2/2005 | Benjamin |
| 6,866,660 B2 | 3/2005 | Garabedian et al. |
| 6,881,211 B2 | 4/2005 | Schweikert et al. |
| 6,887,417 B1 | 5/2005 | Gawreluk et al. |
| 6,939,327 B2 | 9/2005 | Hall et al. |
| 6,939,337 B2 | 9/2005 | Parker et al. |
| 7,018,372 B2 | 3/2006 | Casey et al. |
| 7,025,746 B2 | 4/2006 | Tal |
| 7,037,295 B2 | 5/2006 | Tiernan et al. |
| 7,101,353 B2 | 9/2006 | Lui et al. |
| 7,144,411 B2 | 12/2006 | Ginn et al. |
| 7,169,118 B2 | 1/2007 | Reynolds et al. |
| 7,226,433 B2 | 6/2007 | Bonnette et al. |
| 7,357,794 B2 | 4/2008 | Makower et al. |
| 7,367,967 B2 | 5/2008 | Eidenschink |
| 7,422,571 B2 | 9/2008 | Schweikert et al. |
| 7,438,712 B2 | 10/2008 | Chouinard |
| 7,497,844 B2 | 3/2009 | Spear et al. |
| 7,524,305 B2 | 4/2009 | Moyer |
| 7,540,865 B2 | 6/2009 | Griffin et al. |
| 7,628,769 B2 | 12/2009 | Grandt et al. |
| 7,637,903 B2 | 12/2009 | Lentz et al. |
| 7,645,273 B2 | 1/2010 | Lualdi |
| 7,704,245 B2 | 4/2010 | Dittman et al. |
| 7,713,260 B2 | 5/2010 | Lessard et al. |
| 7,722,567 B2 | 5/2010 | Tal |
| 7,731,694 B2 | 6/2010 | Becker et al. |
| 7,744,571 B2 | 6/2010 | Fisher et al. |
| 7,749,185 B2 | 7/2010 | Wilson et al. |
| 7,766,820 B2 | 8/2010 | Core |
| 7,833,218 B2 | 11/2010 | Lunn et al. |
| 7,837,671 B2 | 11/2010 | Eversull et al. |
| 7,871,398 B2 | 1/2011 | Chesnin et al. |
| 7,905,877 B1 | 3/2011 | Jimenez et al. |
| 7,909,798 B2 | 3/2011 | Osypka |
| 7,963,948 B2 | 6/2011 | Melsheimer |
| 7,968,038 B2 | 6/2011 | Dittman et al. |
| 7,985,213 B2 | 7/2011 | Parker |
| 7,989,042 B2 | 8/2011 | Obara et al. |
| 7,993,305 B2 | 8/2011 | Ye et al. |
| 8,021,409 B2 | 9/2011 | Aggerholm |
| 8,070,898 B2 | 12/2011 | Eversull et al. |
| 8,123,726 B2 | 2/2012 | Searfoss et al. |
| 8,147,452 B2 | 4/2012 | Nardeo et al. |
| 8,206,375 B2 | 6/2012 | Snow |
| 8,231,551 B2 | 7/2012 | Griffin et al. |
| 8,246,574 B2 | 8/2012 | Jacobs et al. |
| 8,257,298 B2 | 9/2012 | Hamboly |
| 8,273,059 B2 | 9/2012 | Nardeo et al. |
| 8,292,827 B2 | 10/2012 | Musbach et al. |
| 8,298,189 B2 | 10/2012 | Fisher et al. |
| 8,303,570 B2 | 11/2012 | Gregorich et al. |
| 8,317,754 B2 | 11/2012 | Leeflang et al. |
| 8,343,136 B2 | 1/2013 | Howat et al. |
| 8,366,720 B2 | 2/2013 | Mitelberg et al. |
| 8,377,035 B2 | 2/2013 | Zhou et al. |
| 8,398,696 B2 | 3/2013 | Buiser et al. |
| 8,475,431 B2 | 7/2013 | Howat |
| 8,529,719 B2 | 9/2013 | Pingleton et al. |
| 8,591,495 B2 | 11/2013 | Fischell et al. |
| 8,597,277 B2 | 12/2013 | Lenker et al. |
| 8,636,270 B2 | 1/2014 | Ostrovsky |
| 8,672,888 B2 | 3/2014 | Tal |
| 8,684,963 B2 | 4/2014 | Qiu et al. |
| 8,728,055 B2 | 5/2014 | Stehr et al. |
| 8,758,402 B2 | 6/2014 | Jenson et al. |
| 8,821,510 B2 | 9/2014 | Parker |
| 8,974,420 B2 | 3/2015 | Searfoss et al. |
| 9,095,684 B2 | 8/2015 | Martinez-Arraras |
| 9,168,359 B2 | 10/2015 | Rowe et al. |

(56) References Cited

U.S. PATENT DOCUMENTS

| | | |
|---|---|---|
| 9,295,809 B2 | 3/2016 | Sheetz |
| 9,320,873 B2 | 4/2016 | Okamura |
| 9,352,116 B2 | 5/2016 | Guo et al. |
| 9,427,551 B2 | 8/2016 | Leeflang et al. |
| 9,492,636 B2 | 11/2016 | Heideman et al. |
| 9,517,323 B2 | 12/2016 | Kimmel et al. |
| 9,539,368 B2 | 1/2017 | Haslinger et al. |
| 9,539,411 B2 | 1/2017 | Cully et al. |
| 9,545,496 B2 | 1/2017 | Hiroshige et al. |
| 9,597,481 B2 | 3/2017 | Ishikawa |
| 9,616,195 B2 | 4/2017 | Lippert et al. |
| 9,622,892 B2 | 4/2017 | Baker et al. |
| 9,629,978 B2 | 4/2017 | Eversull et al. |
| 9,707,373 B2 | 7/2017 | Nielsen |
| 9,884,169 B2 | 2/2018 | Bierman et al. |
| 9,901,706 B2 | 2/2018 | Storbeck et al. |
| 9,937,319 B1 | 4/2018 | Leeflang et al. |
| 9,980,710 B2 | 5/2018 | Seifert et al. |
| 9,981,115 B2 | 5/2018 | Merk et al. |
| 9,987,460 B2 | 6/2018 | Brustad et al. |
| 10,065,015 B2 | 9/2018 | Leeflang et al. |
| 10,076,639 B2 | 9/2018 | Guo et al. |
| 10,086,172 B2 | 10/2018 | Okamura |
| 10,124,151 B2 | 11/2018 | Okamura et al. |
| 2002/0058910 A1 | 5/2002 | Hermann et al. |
| 2002/0072712 A1 | 6/2002 | Nool et al. |
| 2003/0083623 A1 | 5/2003 | Berg et al. |
| 2004/0059296 A1 | 3/2004 | Godfrey |
| 2004/0122360 A1 | 6/2004 | Waldhauser et al. |
| 2004/0267202 A1 | 12/2004 | Potter |
| 2004/0267203 A1 | 12/2004 | Potter et al. |
| 2005/0090802 A1 | 4/2005 | Connors et al. |
| 2005/0149105 A1 | 7/2005 | Leeflang et al. |
| 2005/0182387 A1 | 8/2005 | Webler |
| 2006/0052749 A1 | 3/2006 | Moyer |
| 2006/0095050 A1 | 5/2006 | Hartley et al. |
| 2006/0111614 A1 | 5/2006 | Saadat et al. |
| 2006/0135981 A1 | 6/2006 | Lenker et al. |
| 2006/0161135 A1 | 7/2006 | Vanderwoude |
| 2006/0200110 A1 | 9/2006 | Lentz et al. |
| 2006/0287574 A1 | 12/2006 | Chin |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0306442 A1 | 12/2008 | Bardsley et al. |
| 2009/0043285 A1 | 2/2009 | Stehr et al. |
| 2009/0192463 A1 | 7/2009 | Nardeo et al. |
| 2009/0240202 A1 | 9/2009 | Drasler et al. |
| 2010/0082000 A1 | 4/2010 | Honeck et al. |
| 2010/0228178 A1 | 9/2010 | Mcgraw |
| 2010/0268196 A1 | 10/2010 | Hastings et al. |
| 2010/0305509 A1 | 12/2010 | Osypka et al. |
| 2012/0245527 A1 | 9/2012 | Stephens et al. |
| 2013/0018309 A1 | 1/2013 | Ewing et al. |
| 2013/0131718 A1 | 5/2013 | Jenson et al. |
| 2013/0317438 A1 | 11/2013 | Ellingwood et al. |
| 2013/0317481 A1 | 11/2013 | Ellingwood et al. |
| 2014/0031843 A1 | 1/2014 | Rottenberg et al. |
| 2015/0051541 A1 | 2/2015 | Kanemasa et al. |
| 2015/0174364 A1 | 6/2015 | Kennelly et al. |
| 2015/0201963 A1 | 7/2015 | Snow |
| 2015/0352330 A1 | 12/2015 | Wasdyke et al. |
| 2016/0001042 A1 | 1/2016 | Worley et al. |
| 2016/0051798 A1 | 2/2016 | Weber et al. |
| 2016/0058976 A1 | 3/2016 | Okamura et al. |
| 2016/0066948 A1 | 3/2016 | Ellingwood et al. |
| 2016/0096000 A1 | 4/2016 | Mustapha |
| 2016/0220358 A1 | 8/2016 | Wilson et al. |
| 2016/0346507 A1 | 12/2016 | Jackson et al. |
| 2016/0346508 A1 | 12/2016 | Williams et al. |
| 2016/0354583 A1 | 12/2016 | Ellingwood et al. |
| 2016/0375222 A1 | 12/2016 | Wada |
| 2017/0043135 A1 | 2/2017 | Knutsson |
| 2017/0056063 A1 | 3/2017 | Ellingwood et al. |
| 2017/0072165 A1 | 3/2017 | Lim et al. |
| 2017/0087331 A1 | 3/2017 | Cully et al. |
| 2017/0113018 A1 | 4/2017 | Shimizu et al. |
| 2017/0120008 A1 | 5/2017 | Burkholz et al. |
| 2017/0238965 A1 | 8/2017 | Murphy |
| 2017/0252535 A1 | 9/2017 | Ganske et al. |
| 2017/0274179 A1 | 9/2017 | Sullivan et al. |
| 2017/0281908 A1 | 10/2017 | Ellingwood et al. |
| 2017/0296777 A1 | 10/2017 | Heisel et al. |
| 2017/0333682 A1 | 11/2017 | Nardeo |
| 2017/0340860 A1 | 11/2017 | Eberhardt et al. |
| 2018/0001061 A1 | 1/2018 | Okamura et al. |
| 2018/0015254 A1 | 1/2018 | Cragg et al. |
| 2018/0043138 A1 | 2/2018 | Chu |
| 2018/0056037 A1 | 3/2018 | Shimizu |
| 2018/0228502 A1 | 8/2018 | Shaffer et al. |
| 2018/0250498 A1 | 9/2018 | Stern et al. |
| 2018/0256847 A1 | 9/2018 | Lareau et al. |
| 2018/0344987 A1 | 12/2018 | Lancette et al. |
| 2018/0361116 A1 | 12/2018 | Quick et al. |

FOREIGN PATENT DOCUMENTS

| | | |
|---|---|---|
| EP | 1053039 A1 | 11/2000 |
| EP | 1212185 A1 | 6/2002 |
| EP | 1444000 A2 | 8/2004 |
| EP | 1631343 A1 | 3/2006 |
| EP | 1656963 A1 | 5/2006 |
| EP | 1853331 A2 | 11/2007 |
| EP | 2068994 A2 | 6/2009 |
| EP | 2335764 A1 | 6/2011 |
| EP | 2429628 A2 | 3/2012 |
| EP | 2473123 A1 | 7/2012 |
| EP | 2703069 A2 | 3/2014 |
| EP | 3132823 A1 | 2/2017 |
| EP | 3311873 A1 | 4/2018 |
| EP | 3347079 A1 | 7/2018 |
| EP | 3395301 A1 | 10/2018 |
| GB | 252863 A | 6/1926 |
| JP | 19968257128 | 10/1996 |
| JP | 2004357847 A | 12/2004 |
| JP | 2008543440 A | 12/2008 |
| JP | 4695878 B2 | 6/2011 |
| JP | 5581139 B2 | 8/2014 |
| JP | 04326702 | 9/2020 |
| WO | 93008986 A1 | 5/1993 |
| WO | 93015872 A1 | 8/1993 |
| WO | 97037713 A1 | 10/1997 |
| WO | 2000048659 A2 | 8/2000 |
| WO | 2001041858 A2 | 6/2001 |
| WO | 2006138356 A2 | 12/2006 |
| WO | 2009114556 A2 | 9/2009 |
| WO | 2017094697 A1 | 6/2017 |
| WO | 2018191547 A1 | 10/2018 |

OTHER PUBLICATIONS

International Search Report and Written Opinion in International Application No. PCT/US2017/065046 dated Mar. 22, 2018 (5 pages).

Office Action received in corresponding Indian Application No. 201917026180 dated Sep. 15, 2021, 7 pp.

Written Opinion for corresponding Singapore Application No. 11201905183X dated Sep. 7, 2020 (4 pages).

OVERMOLD TECHNIQUE FOR PEEL-AWAY INTRODUCER DESIGN

CROSS-REFERENCE TO RELATED APPLICATIONS

The present application is a continuation of U.S. patent application Ser. No. 17/741,627, filed May 11, 2022, now U.S. Pat. No. 11,717,640, which is a continuation of U.S. patent application Ser. No. 15/834,783, filed Dec. 7, 2017, now U.S. Pat. No. 11,364,363, which claims the benefit of the filing date of U.S. Provisional Patent Application No. 62/431,671, filed on Dec. 8, 2016, the entire disclosures of which are hereby incorporated herein by reference.

BACKGROUND OF THE INVENTION

Peel-away introducers are disposable medical devices used in a cardiac catheterization or other medical setting to deliver medical devices into the vasculature. Standard peel-away introducers include a proximal plastic hub coupled to a sheath. Medical devices can be inserted through the plastic hub and into the sheath, through which the device can be placed in a patient's body. Intravascular medical devices, such as intracardiac blood pumps, catheters, guidewires, or leads, can be introduced into a patient's vasculature through a peel-away introducer. Once the medical device has been positioned, the peel-away introducer can be removed. In one approach, the operator breaks the introducer by cracking the plastic introducer hub and peeling down the shaft of the sheath body. In order to break the peel-away introducer, the operator grasps the molded hub and breaks it at the proximal end of the sheath along axial notches or scorings. The sheath tears along perforations or scorings down one or both sides of the sheath and can be peeled axially. The peel-away introducer allows the introducer to be removed after a medical device is inserted into a patient through the introducer without disturbing or removing the medical device.

In a common manufacturing technique, peel-away introducers are formed from an extruded plastic tube with axial notches in a hub body. A hub body including notches and/or wings to facilitate breaking is overmolded onto an extruded plastic sheath or tube. The plastic tube is first assembled over a corepin or mandrel which defines and maintains the inner cavity of the hub and inner diameter and geometry of the sheath. The mandrel and extruded sheath are then placed into a mold cavity allowing for molten plastic to be injected and cooled, creating the plastic hub that the user breaks to initiate peeling.

In the overmolding technique, after the mandrel and extruded sheath are placed into a mold, molten plastic in injected into the mold. The plastic cools around the sheath in the shape of the mold, forming the hub body. The injected plastic is maintained at a high temperature when it is introduced to the mold, and the heat from the injected plastic surrounding the sheath may be sufficient to heat a top layer of the sheath plastic such that the plastic of the sheath may start to flow in a process called reflowing. The portion of the sheath disposed inside the hub of the assembly may lose its internal scoring or notching during the molding process if the heat of the injected plastic reflows into one or more of the scores/notches. As a result, the forces required to break the hub may be excessive or inconsistent because the sheath does not include a weakened section of one of the scores/notches. Furthermore, when the plastic of the sheath is reflowed and the scoring is removed in the section of the sheath within the hub, there is an increased risk that during the breaking of the hub the tear will not propagate to the scoring in the sheath body outside the section in the overmolded hub leading to a defective peel-away introducer sheath.

SUMMARY OF THE INVENTION

Described herein are methods and systems for producing a peel-away introducer including an overmolded hub while maintaining the scoring of the sheath. During overmolding, a mandrel designed with outer surface protrusions on which the sheath is assembled, maintains the inner scorings of the sheath through the injection molding process despite the application of extreme heat. With the internal scorings of the sheath maintained, when the hub is broken by an operator, the proximal section of the sheath tube in the overmolded hub breaks more easily and with less required force. Sheaths manufactured by the methods disclosed herein can also peel more easily.

In one aspect, a method for manufacturing a medical introducer includes placing an introducer sheath onto a mandrel, and overmolding an introducer hub onto a proximal end of the introducer sheath. The introducer sheath has one or more score lines formed on an inner surface. The mandrel has a number of surface protrusions so that when the introducer sheath is positioned on the mandrel, each of the surface protrusions contacts one of the score lines formed on the introducer sheath and prevents plastic material from the introducer hub from contacting the score lines.

In some implementations, the number of surface protrusions on the mandrel is equal to the number of score lines formed on the sheath. In some implementations, the introducer hub includes a number of notches. In some implementations, the number of notches in the introducer hub is equal to the number of score lines formed on the sheath and also equal to the number of surface protrusions on the mandrel. In some implementations, at least one of the number of notches is aligned with a score line formed on the sheath. In some implementations, at least two notches are aligned with a score line formed on the sheath. In some implementations, the introducer hub and introducer sheath are configured to be broken into at least two pieces along the notches and score lines.

In some implementations, the number of surface protrusions on the mandrel is not equal to the number of score lines formed on the sheath. In some implementations, at least one of the number of score lines formed on the inner surface of the introducer sheath is removed during the overmolding. In some implementations, the number of surface protrusions on the mandrel is equal to a desired number of score lines in the sheath.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION OF THE DRAWINGS

Following below are more detailed descriptions of various concepts related to inventive methods of manufacturing a peel-away medical introducer. It should be appreciated that various concepts introduced above and discussed in greater detail below may be implemented in any number of ways, as the disclosed concepts are not limited to any particular manner of implementation. For example, though peel-away introducer sheaths are depicted herein having two axial notches which divide the introducer hub and underlying sheath into two sections, the introducer hub and sheath may be manufactured to have any number of axial notches or perforations so as to allow parting into any number of portions along an axial direction. Furthermore, although surface protrusions of a mandrel are described with reference to maintaining score lines on a sheath for use in a peel-away introducer, the surface protrusions on the mandrel may be used to protect other features of the internal geometry of a sheath during any overmolding or heat-treating process. Examples of implementations and applications are provided primarily for illustrative purposes.

The methods and systems described herein enable production of a peel-away introducer including an overmolded hub while maintaining the scoring of the sheath. The mandrel for holding the hub and the sheath can have one or more outer elongate protrusions formed along an outer surface thereof. A protrusion can contact each of the corresponding inner scorings of the sheath so that when heat is applied the score lines are maintained through the injection molding process rather than filled with material from the hub or the sheath (e.g., plastic that has melted during heat application). With the internal scorings of the sheath maintained, when the hub is broken by an operator, the proximal section of the sheath tube in the overmolded hub breaks more easily and with less required force than if this material had flowed into the score lines and hardened. Additionally, with the score lines in the introducer sheath maintained, the hub can be broken and the sheath peeled longitudinally to facilitate removal of the introducer hub assembly. The overmolding method described herein promotes appropriate breaking of the introducer hub and peeling of the sheath as designed.

Figure 1A:
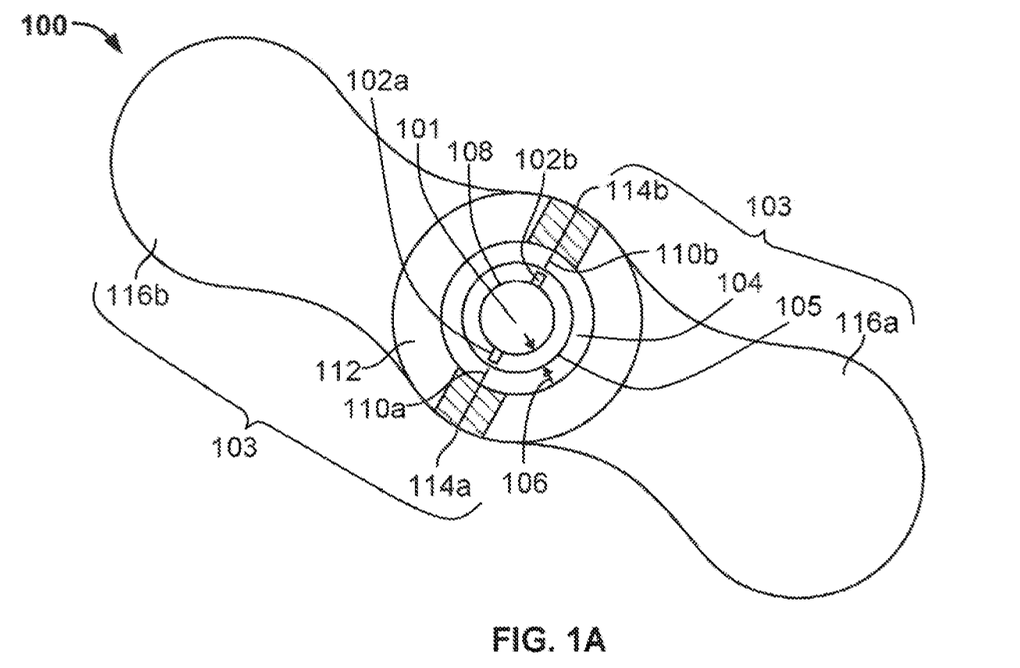
FIG. 1A shows a top view of an introducer hub molded over a sheath during the manufacture process according to an embodiment.

FIG. 1A shows a top view of an introducer hub and mandrel assembly 100 including a hub body 112 molded over an introducer sheath 104 during the manufacture process. The introducer hub assembly 103 includes an introducer sheath 104, a first score line 110a, a second score line 110b, a hub body 112, a first notch 114a, a second notch 114b, a first wing 116a, and a second wing 116b. The first score line 110a and the second score line 110b are on opposite sides of the introducer sheath 104. The introducer sheath 104 is positioned over a mandrel 101 (also called a corepin) having a first surface protrusion 102a and a second surface protrusion 102b on opposite sides of the mandrel 101. The first surface protrusion 102a and the second surface protrusion 102b are configured to coincide with the first score line 110a and the second score line 110b in the introducer sheath 104. After the introducer sheath 104 is positioned over the mandrel 101 with the first surface protrusion 102a and the second surface protrusion 102b aligned with the first score line 110a and the second score line 110b in the introducer sheath 104, the introducer hub body 112 can be overmolded over the proximal end of the introducer sheath 104. The first notch 114a and the second notch 114b are aligned with the first score line 110a and the second score line 110b in the introducer sheath 104 to facilitate breaking of the introducer hub assembly 103.

The mandrel 101 with the first surface protrusion 102a and the second surface protrusion 102b is shaped to maintain the inner geometry of the introducer sheath 104. The introducer sheath 104 fits tightly over the mandrel 101 in preparation for overmolding of the introducer hub assembly 103. There may be some distance 106 between an outer surface 108 of the mandrel 101 and an inner surface 105 of the introducer sheath 104, but in most cases the distance 106 is minimized such that the outer surface 108 of the mandrel 101 is in contact with the inner surface 105 of the introducer sheath 104 in areas which are to be protected during overmolding, such as at the first score line 110a and the second score line 110b. In some implementations, the distance 106 between the outer surface 108 of the mandrel 101 and the inner surface 105 of the introducer sheath 104 in areas which are not protected during overmolding is e.g., 0 mm, 0.1 mm, 0.2 mm, 0.3 mm, or 0.4 mm or it can be structured at any other suitable distance. The surface protrusions 102a and 102b may be set at a desired height from the body of the mandrel 101. In some implementations, the surface protrusions 102a and 102b extend from the surface of the mandrel 101 by about 0.05 mm, 0.1 mm, 0.2 mm, 0.3 mm, or any suitable height. In certain embodiments, the distance between the outer surface 108 of the mandrel 101 and an inner surface 105 of the introducer sheath 104 is between about 0 mm and 0.4 mm, while the protrusions extend from the outer surface 108 of the mandrel 101 and have a height of about 0.05 mm to 0.3 mm. In some implementations, the surface protrusions have a shape which is square, rectangular, cylindrical, or any other suitable shape. In some implementations, the protrusions extend longitudinally along the mandrel. In some implementations, the protrusions extend in a helix along the mandrel.

With the introducer sheath 104 fit over the mandrel 101, the introducer hub assembly 103 can be formed onto the sheath 104 such as by being injection molded over the introducer sheath 104. The injection molding process exposes the proximal end of the introducer sheath 104 to high temperatures and/or pressures which can cause reflow of the plastic from which the introducer sheath 104 is formed. Reflowing plastic may cover or completely fill the first score line 110a and the second score line 110b in the introducer sheath 104 if the first score line 110a and the second score line 110b are not protected by a corresponding protrusion. The first surface protrusion 102a and the second surface protrusion 102b extend into the first score line 110a and the second score line 110b such that even if the introducer sheath 104 is heated and reflow occurs, the first score line 110a and the second score line 110b are maintained.

If the first score line 110a and the second score line 110b are altered or removed by reflow of the plastic during construction, the introducer sheath 104 may not separate properly during breaking of the introducer hub assembly 103 after use. The hub body 112 may break as designed at first notch 114a and second notch 114b when an outward or downward force is applied to the first wing 116a and second wing 116b. However, if the first score line 110a and the second score line 110b have been damaged, the separation may not propagate to the introducer sheath 104, or from a proximal portion of the introducer sheath 104 to a more distal portion not in contact with the introducer hub assembly 103. As a result, it may be difficult or uncomfortable for an operator to apply the additional or excessive force required in order to initiate the breaking of the introducer hub assembly 103.

Though the introducer sheath 104 is depicted here having two score lines, the first score line 110a and the second score line 110b, the introducer sheath 104 may be configured with any number of score lines. In some implementations, the introducer sheath is configured with one score line, two score lines, three score lines, four score lines, six score lines, ten score lines, or any other suitable number of score lines. The score lines may be formed as perforations, scorings, indentations or by any other suitable means.

The mandrel 101 is depicted here having two surface protrusions, the first surface protrusion 102a and the second surface protrusion 102b, but may have any suitable number of surface protrusions. In some implementations, the mandrel 101 has one surface protrusion, two surface protrusions, three surface protrusions, four surface protrusions, six surface protrusions, or any other suitable number of surface protrusions. The mandrel 101 may have a number of surface protrusions equal to the number of score lines on the introducer sheath 104. Alternatively, the mandrel 101 may have a number of surface protrusions which is less than the number of score lines on the introducer sheath 104. If the number of surface protrusions is less than the number of score lines on the introducer sheath 104, any additional score lines on the introducer sheath 104 may be removed by reflow of material during the manufacture of the introducer hub assembly 103 overlay. For example, if an introducer sheath 104 has three score lines, but only two are desired for an introducer hub assembly a mandrel with only two surface protrusions may be used to protect two of the three score lines on the introducer sheath during overmolding. Alternatively, the mandrel 101 may have a number of surface protrusions that is greater than the number of score lines on the introducer sheath 104 such that only some of the total surface protrusions contact the score lines. This can allow, for example, the mandrel 101 to be configured to assemble sheaths having varying number of score lines.

Figure 1B:
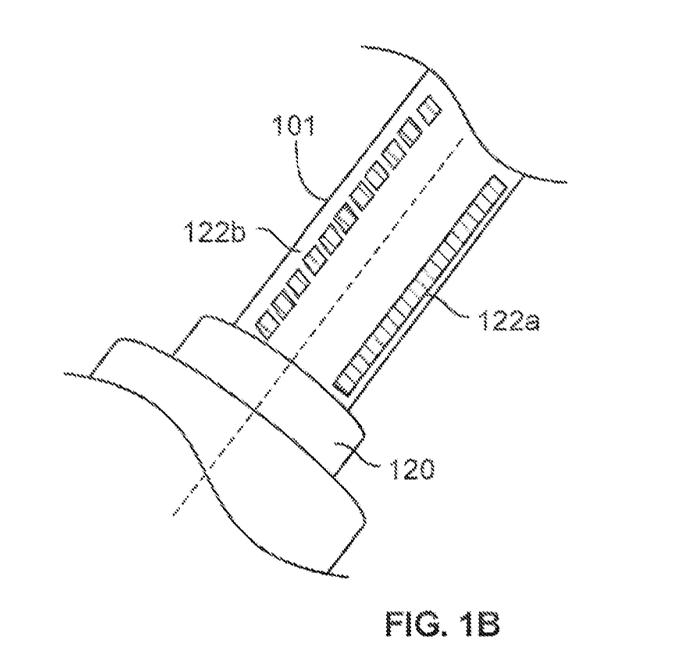
FIG. 1B shows a perspective view of a mandrel having both continuous surface protrusions and surface protrusions configured as a series of protrusions.

The surface protrusions on the mandrel 101 may be matched to the type of score lines on the introducer sheath 104, as shown in FIG. 1B. FIG. 1B includes a mandrel 101 extending from a base 120 with a first surface protrusion 122a and a second surface protrusion 122b. The first surface protrusion 122a is configured as a continuous protrusion from the outer surface of the mandrel 101 which would contact a score line of an introducer sheath along an entire length without interruption. The second surface protrusion 122b is configured as a series of surface protrusions arranged in a line along the mandrel 101. The second surface protrusion 122b contacts the introducer sheath only at each of the individual protrusions, and not at the space between the protrusions. For example, a series of surface protrusions such as second surface protrusion 122b may be used to protect a score line configured as a perforation.

Figure 2:
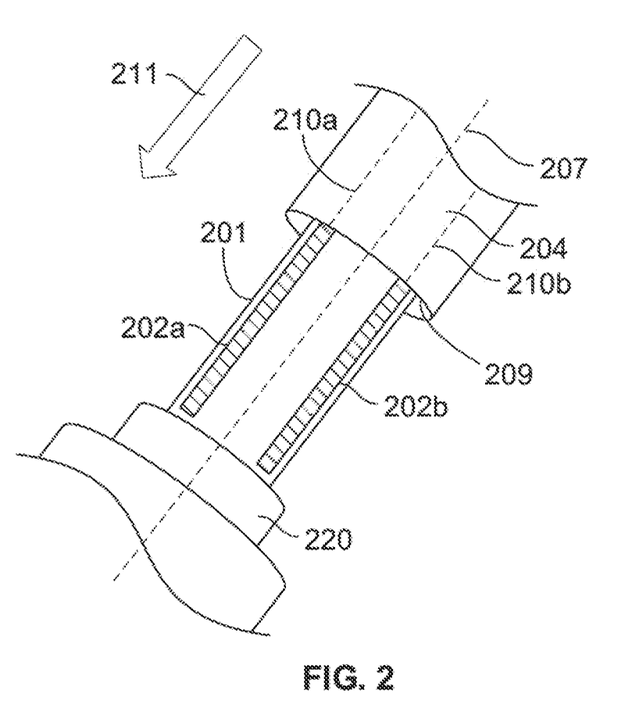
FIG. 2 shows a perspective view of a mandrel being inserted into a sheath during the manufacture process according to an embodiment.

FIG. 2 shows a perspective view of a mandrel 201 partially inserted into an introducer sheath 204 in preparation for overmolding of an introducer hub. The mandrel 201 includes a base 220, a first surface protrusion 202a and a second surface protrusion 202b. The first surface protrusion 202a and a second surface protrusion 202b are parallel to a longitudinal axis 207 of the mandrel 201. The introducer sheath 204 includes a proximal end 209, a first score line 210a and a second score line 210b aligned parallel to the longitudinal axis 207 of the mandrel 201 which coincides with a longitudinal axis 207 of the introducer sheath 204 which the introducer sheath 204 is placed on the mandrel 201. The first surface protrusion 202a and a second surface protrusion 202b are aligned with the first score line 210a and the second score line 210b of the introducer sheath 204 in order to protect the score lines and internal geometry of the introducer sheath 204 during overmolding of an introducer hub at the proximal end 209 of the introducer sheath 204. Introducer sheath 204 is inserted over the mandrel 201 in the direction of arrow 211 prior to the overmolding of the introducer hub.

Figure 3:
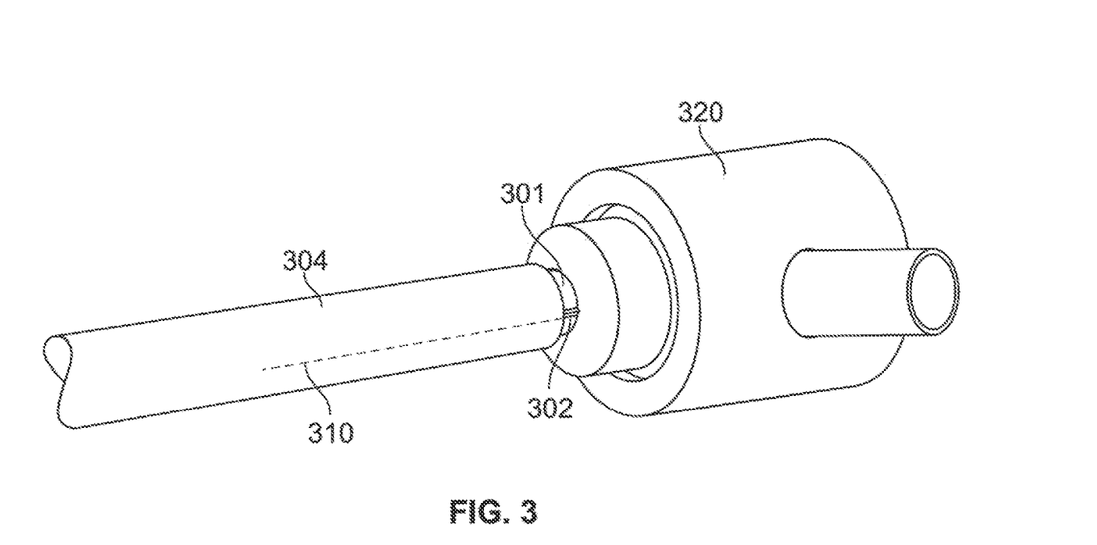
FIG. 3 shows a perspective view of a mandrel fully inserted into a sheath during the manufacture process according to an embodiment.

FIG. 3 shows a perspective view of a mandrel 301 fully inserted into an introducer sheath 304 in a final configuration prior to overmolding of an introducer hub onto the introducer sheath 304. The mandrel 301 includes a base 320 and one or more surface protrusions 302. The introducer sheath 301 includes a first score line 310 aligned parallel to a longitudinal axis 307 of the introducer sheath 304. The surface protrusion 302 is aligned with the first score line 310 to protect the first score line 310 from reflow during further processing. The introducer sheath 304 is designed to tear along the first score line 310 when the introducer hub assembly is broken. However, the first score line 310 may become damaged or be removed by the heat from the overmolding of the introducer hub body if the first score line 310 and any other score lines are not protected and maintained. The surface protrusion 302 of the mandrel 301 protects the internal geometry of the introducer sheath 304 including the first score line 310 during the overmolding of the introducer hub body so that the first score line 310 remains. The mandrel 301 is sized to fit inside the introducer sheath 304 and the surface protrusion 302 on the mandrel is likewise sized to align with and correspond to the first score line 310 on the introducer sheath 304.

Figure 4:
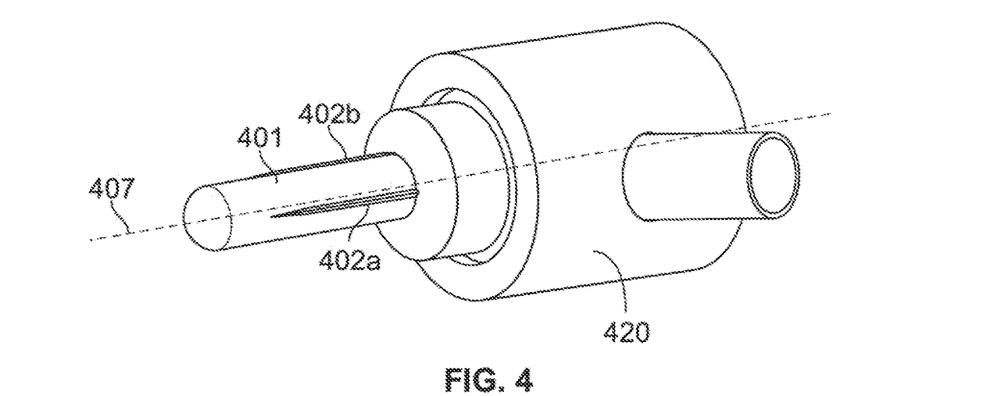
FIG. 4 shows a perspective view of a mandrel having a surface protrusion according to an embodiment.

FIG. 4 shows a perspective view of a mandrel 401 having surface protrusions 402a and 402b. The mandrel 401 includes a base 420, a first surface protrusion 402a, and a second surface protrusion 402b. The first surface protrusion 402a and the second surface protrusion 402b extend along the cylindrical mandrel 401 parallel to the longitudinal axis. The first surface protrusion 402a and the second surface protrusion 402b are sized and positioned to correspond to the internal geometry and score lines of the introducer sheath so that the internal geometry and space of the introducer sheath is maintained during the manufacture of the introducer hub on the introducer sheath.

Although two surface protrusions 402, the first surface protrusion 402a and the second surface protrusion 402b, are shown in FIG. 4, the mandrel 401 can have any suitable number or orientation of surface protrusions to protect and maintain score lines on an introducer sheath placed over the mandrel 401. The mandrel 401 may have one, two, three, four, six, eight, or any suitable number of surface protrusions. In some implementations, the mandrel 401 includes the same number of surface protrusions as the number of score lines on the introducer sheath. In some implementations, the mandrel 401 includes a smaller number of surface protrusions than the number of score lines on the introducer sheath. In such cases, the additional score lines on the introducer sheath will be removed by reflow of the plastic of the sheath during the overmolding process. Removal of unnecessary score lines during overmolding by not protecting the score lines with the mandrel may allow multiple styles of introducer hub assemblies to be prepared using a single type of introducer sheath. The surface protrusions may be aligned along the longitudinal axis 407 as shown here, or they may be oriented at an angle to the longitudinal axis or in a spiral orientation around the outer surface of the mandrel.

The first surface protrusion 402a and the second surface protrusion 402b shown in FIG. 4 are depicted as continuous raised sections of the mandrel 401. In some implementations, the surface protrusions on the mandrel 401 are configured as a series of raised dots in order to protect the specific geometry of the interior of the introducer sheath. In some implementations, the surface protrusions may be a continuous raised section configured as a ridge with an angled top, a squared top or a rounded top. The shape of the surface protrusions may be matched to a shape of the score lines in the introducer sheath.

Figure 5:
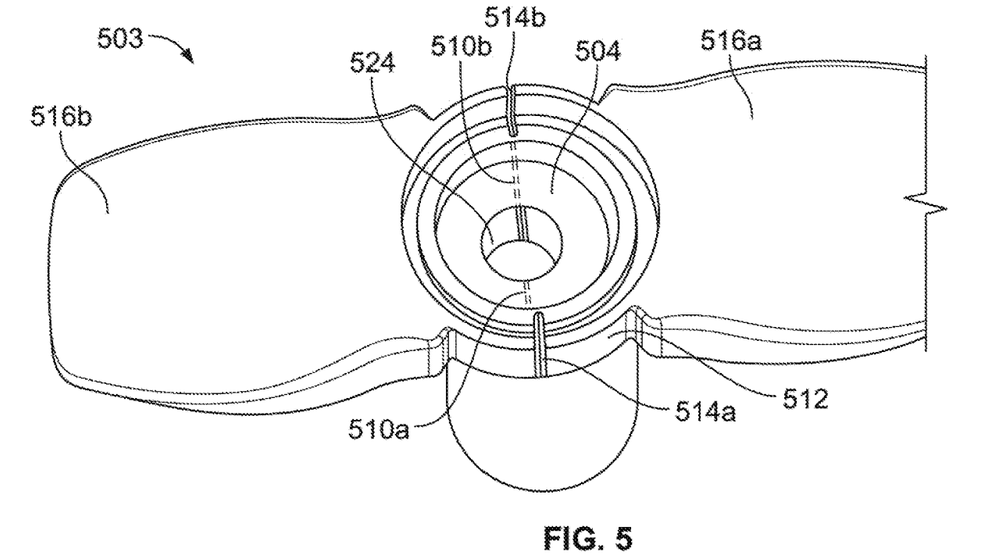
FIG. 5 shows a perspective view of a peel-away introducer hub assembly according to an embodiment.

FIG. 5 shows a perspective view of a peel-away introducer hub assembly 503. The peel-away introducer hub assembly 503 includes a hub body 512, a first wing 516a, a second wing 516b, a first notch 514a, a second notch 514b, an introducer sheath 504, a first score line 510a, a second score line 510b, and a throughgoing cavity 524. The first notch 514a is aligned with the first score line 510a, and the second notch 514b is aligned with the second score line 510b. The first wing 516a and the second wing 516b extend on opposite sides of the hub body 512, such that the first notch 514a and the second notch 514b are positioned between the first wing 516a and the second wing 516b.

A medical device or catheter may be inserted into a patient through the throughgoing cavity 524 in the introducer hub assembly 503. After the device or catheter has been inserted, an operator can break the introducer hub assembly 503 by applying a force to the first wing 516a and the second wing 516b, breaking the introducer hub assembly 503 into two or more pieces. The introducer hub assembly 503 is designed to break at the first notch 514a and the second notch 514b upon the application of this force on the first wing 516a and the second wing 516b. The alignment of the first notch 514a and the second notch 514b with the first score line 510a and the second score line 510b, respectively, allows the break force applied by the operator to break the hub body 512 to propagate from the first notch 514a to the first score line 510a and from the second notch 514b to the second score line 510b to allow the introducer hub assembly 503 to be broken into two pieces and the introducer sheath 504 to be peeled away. Good alignment of the notches with the score lines that have been protected from damage during the overmolding of the hub body 512 allows the introducer hub assembly to be easily broken and peeled with a nominal breaking force applied.

Figure 6:
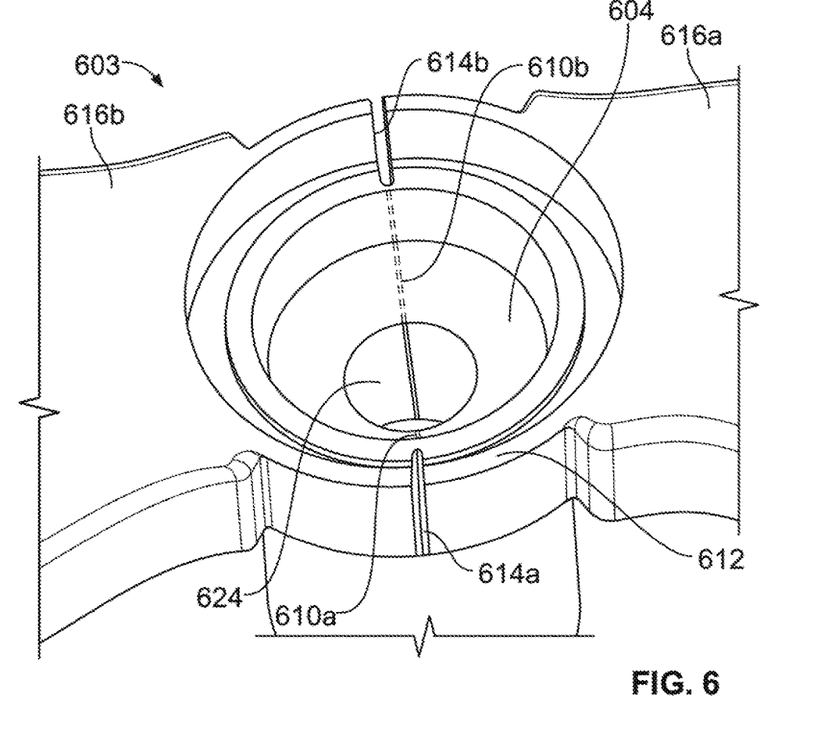
FIG. 6 shows an alternative view of a peel-away introducer hub according to an embodiment.

FIG. 6 shows an alternative view of the peel-away introducer hub 503 of FIG. 5, illustrating the alignment of the second notch 614b with the second score line 610b opposite the first notch 614a and first score line 610a. The first wing 616a, second wing 616b, and cavity 624 of FIG. 6 are the same features described above with respect to first wing 516a, second wing 516b, and cavity 524 of FIG. 5, respectively. The alignment of the second notch 614b with the second score line 610b (and first notch 614a and first score line 610a) allows the transfer of the breaking force from the hub body 612 to the introducer sheath 604. If the score line 610 of the introducer sheath 604 has not been damaged or removed by the flow of plastic material from the introducer sheath 604 during the overmolding of the introducer hub body 612, the force may be propagated from the hub body 612 to the introducer sheath 604 without incident.

If the score line 610 of the introducer sheath 604 has been damaged or removed by the reflow of plastic material from the introducer sheath 604 during overmolding, the introducer sheath 604 may not easily split apart at the hub body 612 or below the hub body 612. This may require additional or excessive force to be applied to the hub body 612 or to the introducer sheath 604 in order to break the hub body 612 and introducer sheath. Alternatively, the malfunction of the introducer hub assembly 603 due to damaged score lines in the introducer sheath 604 may result in a defective introducer hub assembly which cannot be peeled away as designed. Alternative or suboptimal methods for removal may then be used which may require additional tools.

Figure 7:
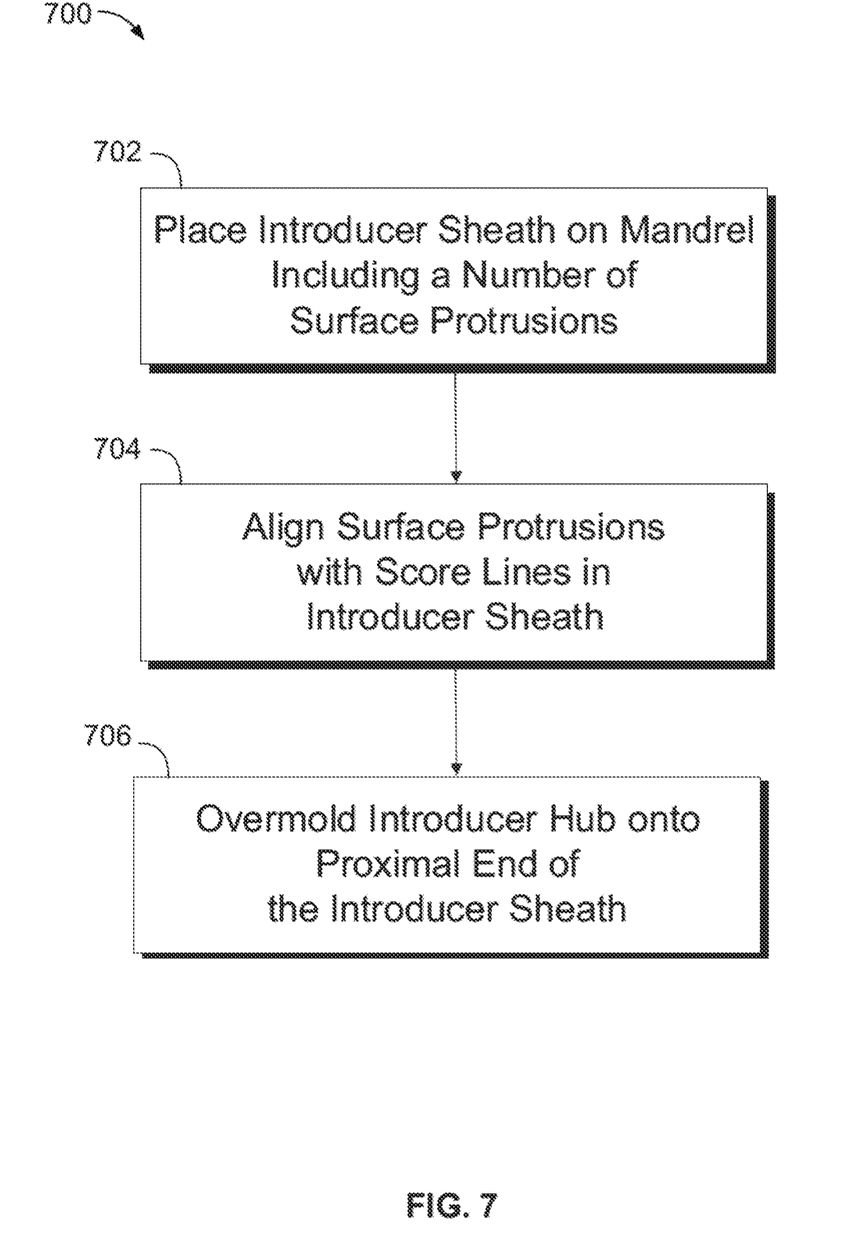
FIG. 7 shows a method for manufacturing a peel-away introducer hub according to an embodiment.

FIG. 7 shows a method 700 for manufacturing a peel-away introducer hub, such as the introducer hub assembly 103 of FIG. 1A, hub assembly 503 of FIG. 5, or any other suitable hub assembly. At step 702 the method includes placing an introducer sheath on a mandrel including a number of surface protrusions. The surface protrusions are designed to contact score lines in an interior surface of the introducer sheath in order to protect the geometry of the interior of the introducer sheath including the score lines. The mandrel may include the same number of surface protrusions as the number of score lines on the introducer sheath, or in some implementations, the mandrel includes a smaller number of surface protrusions if a number of score lines are designed to be removed during the next step. The mandrel and extruded sheath are then placed into a mold cavity allowing for molten plastic to be injected and cooled.

At step 704, the surface protrusions of the mandrel are aligned with the score lines of the introducer sheath. The introducer sheath fits tightly over the mandrel and the score lines on the interior of the introducer sheath are in contact with the surface protrusions of the mandrel. In some implementations, the surface protrusions of the mandrel may be aligned with the score lines of the introducer sheath before the mandrel is inserted into the introducer sheath, or simultaneous to insertion. The shape, size, and height of the surface protrusions may be matched to the score lines in the introducer sheath. In some implementations, the surface protrusions may be a continuous raised section configured as a ridge with an angled top, a squared top or a rounded top. The surface protrusions on the mandrel may be a variety of heights from the body of the mandrel to match the score lines in the introducer sheath. In some implementations, the surface protrusions extend from the surface of the mandrel by 0.05 mm, 0.1 mm, 0.2 mm, 0.3 mm, or any suitable height. In some implementations, there is some distance between an outer surface of the mandrel and an inner surface of the introducer sheath, but in most cases the distance is minimized such that the outer surface of the mandrel is in contact with the inner surface of the introducer sheath at least in regions which are to be protected from reflow during further manufacture. In some implementations, the distance between the outer surface of the mandrel and the inner surface of the introducer sheath in areas which are not to be protected is 0 mm, 0.1 mm, 0.2 mm, 0.3 mm, 0.4 mm or any other suitable distance. In some implementations, the surface protrusions 102*a* and 102*b* extend from the surface of the mandrel 101 by about 0.05 mm, 0.1 mm, 0.2 mm, 0.3 mm, or any suitable height. In certain implementations, the distance between the outer surface of the mandrel and an inner surface of the introducer sheath is between about 0 mm and 0.4 mm, while the protrusions extend from the outer surface of the mandrel and have a height of about 0.05 mm to 0.3 mm.

At step 706, the method includes overmolding an introducer hub onto a proximal end of the introducer sheath. The overmolding process uses heating, which may cause the plastic material of the introducer sheath to melt and reflow. The areas of the score lines which are protected by their contact with the surface protrusions of the mandrel are not covered by reflowing plastic and are maintained throughout the overmolding process. Areas which are not protected by the surface protrusions on the mandrel may reflow and fill in any additional score lines.

The overmolding of the introducer hub may also include overmolding one or more wings onto the introducer hub to aid in the breaking of the hub after use. After the introducer hub is overmolded onto the proximal end of the sheath the introducer hub and introducer sheath are removed from the mandrel. The introducer sheath includes a number of score lines which have been maintained by the mandrel during the overmolding of the introducer hub and introducer hub body. The score lines correspond to notches in the overmolded introducer hub. The introducer hub may be separated into two or more pieces at the notches and score lines after use with the application of a nominal force on the wings. Once the introducer hub has been separated at the notches and score lines, the introducer sheath may be peeled away along the score lines to remove the introducer hub assembly.

The foregoing is merely illustrative of the principles of the disclosure, and the methods and systems can be practiced other than the described implementations, which are represented for purposes of illustration and not of limitation. It is to be understood that the methods and systems disclosed herein, while shown for use in manufacture of a peel-away introducer hub and sheath, may be applied to other systems in which internal geometries of a sheath must be maintained during heat treatment.

Variations and modifications will occur to those of skill in the art after reviewing this disclosure. For example, the geometries and orientations of the surface protrusions of the mandrel can be beneficially chosen to match an internal geometry of the introducer sheath, or to complement an internal geometry or desired internal geometry. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitution, and alterations are ascertainable by one skilled in the art and could be made without departing from the scope of the information disclosed herein.

The invention claimed is:

1. A method of manufacturing a medical introducer, comprising:

placing an introducer sheath on a mandrel, the introducer sheath having a plurality of score lines formed on an inner surface thereof, the introducer sheath having more than one type of score line; the mandrel including a plurality of surface protrusions; and overmolding a plastic material onto a proximal end of the introducer sheath to form an introducer hub using a mold surrounding the proximal end of the introducer sheath, wherein, when the introducer sheath is positioned on the mandrel, each of the plurality of surface protrusions matches a type of corresponding score line.

2. The method of claim 1, wherein a number of the plurality of surface protrusions on the mandrel is equal to a number of the plurality of score lines formed on the introducer sheath.

3. The method of claim 2, wherein the introducer hub includes a number of notches.

4. The method of claim 3, wherein the number of notches is both equal to the number of the plurality of score lines formed on the introducer sheath and equal to the number of the plurality of surface protrusions on the mandrel.

5. The method of claim 4, wherein at least one notch of the number of notches is aligned with one score line of the plurality of score lines formed on the introducer sheath.

6. The method of claim 5, wherein the introducer hub includes at least a first notch and a second notch, the first notch being aligned with a first score line of the plurality of score lines formed on the introducer sheath, and the second notch being aligned with a second score line of the plurality of score lines formed on the introducer sheath.

7. The method of claim 6, wherein the introducer hub and the introducer sheath are both configured to be broken into at least two pieces along the first and second notches and the first and second score lines.

8. The method of claim 1, wherein a number of the plurality of surface protrusions on the mandrel is not equal to a number of the plurality of score lines formed on the introducer sheath.

9. The method of claim 8, wherein at least one score line of the plurality of score lines formed on the inner surface of the introducer sheath is removed during the overmolding.

10. The method of claim 9, wherein the number of the plurality of surface protrusions on the mandrel is less than the number of the plurality of score lines formed on the introducer sheath.

11. An introducer hub manufacturing assembly, the assembly comprising:

an introducer sheath formed as a cylindrical tube having a first end and a second end, the introducer sheath including on an inner surface thereof a plurality of score lines extending from the first end to the second end, the introducer sheath having more than one type of score line;

a mold surrounding a first end of the introducer sheath and configured to enable overmolding of a plastic material onto the first end of the introducer sheath to form a hub; and a mandrel inserted into the introducer sheath, wherein the mandrel includes a plurality of surface protrusions on an exterior surface that extends along a length of the mandrel, each of the plurality of surface protrusions being aligned with a corresponding score line, wherein each of the plurality of surface protrusions matches a type of the corresponding score line.

12. The assembly of claim 11, wherein the plurality of surface protrusions extend longitudinally down the mandrel.

13. The assembly of claim 11, wherein at least one of the plurality of surface protrusions is configured as a continuous protrusion.

14. The assembly of claim 11, wherein at least one of the plurality of surface protrusions is configured as a series of protrusions extending down a length of the mandrel.

15. The assembly of claim 11, wherein the hub is formed from a heated plastic.

16. The assembly of claim 15, wherein the introducer sheath is formed from a plastic which reflows when subject to heat above a melting temperature of the plastic.

17. The assembly of claim 11, wherein the hub includes a first notch and a second notch arranged at opposite sides of the hub.

18. The assembly of claim 17, wherein the hub is configured to break at the first notch and the second notch.

19. The assembly of claim 11, wherein the introducer sheath is configured to tear along at least one of the plurality of score lines when the hub is broken.

20. The assembly of claim 11, wherein a number of the plurality of surface protrusions is greater than a number of the plurality of score lines.

21. The assembly of claim 11, wherein a number of the plurality of surface protrusions is less than a number of the plurality of score lines.

22. The assembly of claim 11, wherein a number of the plurality of surface protrusions is equal to a number of the plurality of score lines.

* * * * *